United States Patent [19]

Howard, III et al.

[11] Patent Number: 5,713,847
[45] Date of Patent: Feb. 3, 1998

[54] HUMAN DRUG DELIVERY DEVICE FOR TINNITUS

[75] Inventors: Matthew A. Howard, III; Timothy M. McCulloch, both of Iowa City, Iowa; Carol A. Bauer, Houston, Tex.

[73] Assignee: The University of Iowa Research Foundation, Iowa City, Iowa

[21] Appl. No.: 597,348

[22] Filed: Feb. 6, 1996

Related U.S. Application Data

[60] Division of Ser. No. 332,755, Nov. 1, 1994, which is a continuation-in-part of Ser. No. 194,017, Feb. 9, 1994, Pat. No. 5,496,369.

[51] Int. Cl.$^6$ .................................................. A61N 1/30
[52] U.S. Cl. ................................... 604/21; 607/116
[58] Field of Search ............................ 604/21; 607/3, 607/55, 115, 116, 120, 124, 137; 128/642

[56] References Cited

U.S. PATENT DOCUMENTS

| | | | |
|---|---|---|---|
| 4,357,497 | 11/1982 | Hochmair et al. | 179/107 E |
| 4,850,359 | 7/1989 | Putz | 607/116 |
| 5,000,194 | 3/1991 | Honert et al. | 128/784 |
| 5,271,397 | 12/1993 | Seligman et al. | 607/137 |
| 5,328,460 | 7/1994 | Lord et al. | 604/67 |
| 5,429,582 | 7/1995 | Williams | 607/3 |
| 5,496,369 | 3/1996 | Howard, III | 623/10 |

FOREIGN PATENT DOCUMENTS

| | | | |
|---|---|---|---|
| 0158397 | 10/1985 | European Pat. Off. | 604/21 |
| 0259906 | 3/1988 | European Pat. Off. | 623/11 |

OTHER PUBLICATIONS

Bak, M. et al., "Visual Sensations Produced by Intracortical Microstimulation of the Human Occipital Cortex," Med. Biol. Eng. Comput. 28:257–259 (1990).

Brindley, G.S., et al., "The Sensations Produced by Electrical Stimulation of the Visual Cortex," J. Physiol. 196:479–493 (1968).

Center for Integrated Sensors and Circuits, "Passive Multichannel Recording and Stimulating Electrode Arrays: A catalog of Available Designs," (Jul. 1991).

Cohen, et al., "A Prospective, Randomized Study of Cochlear Implants," N.E.J. of Med. 328(4):233–237 (Jan. 1993).

Damasio et al., "Three–dimensional in Vivo Mapping of Brain Lesions in Humans," Arch. Neurol. 49:137–143 (Feb. 1992).

Dobelle et al., "A Prosthesis for the Deaf Based on Cortical Stimulation," Ann. Otol. 82:445–463 (1973).

Dobelle et al., "Artificial Vision for the Blind: Electrical Stimulation of Visual Cortex Offers Hope for a Functional Prosthesis," Science 183:440–444 (1974).

Drake, K.L., et al., "Performance of Planar Multisite Microprobes in Recording Extracellular Single–unit Intracortical Activity," IEEE Trans. BME 35:719–732 (1988).

Eisenberg et al., "Electrical Stimulation of the Auditory Brain Stem Structure in Deafened Adults," J. Rehab. Res. 24(3):9–22 (1987).

Hitselberger, W.E., et al., "Cochlear Nucleus Implant," Otolaryngol. Head Neck Surg. 92:52–54 (1984).

(List continued on next page.)

*Primary Examiner*—William E. Kamm
*Attorney, Agent, or Firm*—Fleshner & Kim

[57] ABSTRACT

A neural prosthetic drug delivery apparatus for reducing or eliminating the effects of tinnitus. The apparatus includes a catheter which is inserted into the patient's auditory cortex or thalamus. The catheter microinfuses drugs which suppress or eliminate abnormal neural activity into geometrically separate locations of the patient's brain, thereby reducing or eliminating the effects of tinnitus. In one embodiment the apparatus includes a stimulation device for outputting processed electrical signals and an electrode having a plurality of electrical contacts which is arranged in a target zone of the patient's brain. Each of the plurality of electrical contacts independently outputs electrical discharges in accordance with the electrical signals.

19 Claims, 12 Drawing Sheets

OTHER PUBLICATIONS

Martuza, R.L. et al., "Neurofibromatosis 2 (Bilateral Acoustic Neurofibromatosis)," N.Engl. J. Med. 318:684–688 (1988).

Medtronic, "The ITREL®II, The third generation of excellence," (1991).

Morgan, "The First Reported Case of Electrical Stimulation of the Human Brain," J. Hist. Med., pp. 51–63 (Jan. 1982).

Penfield et al., "Somatic Motor and Sensory Representation in the Cerebral Cortex of Man as Studied by Electrical Stimulation," Brain 60:389–443 (1937).

Penfield, W., et al., "Epilepsy and the Functional Anatomy of the Human Brain," Little, Brown and Company, Boston (1954).

Penfield, et al., "The Brain's Record of Auditory and Visual Experience," Brain 86:596–6906 (1963).

Walker, "The Development of the Concept of Cerebral Localization in the Nineteenth Century," Bulletin His. Med. 31(2):99–121 (Mar.–Apr. 1957).

HUMAN DRUG DELIVERY DEVICE FOR TINNITUS

CROSS-REFERENCE TO RELATED APPLICATIONS

This application is a division of U.S. patent application Ser. 08/332,755, filed Nov. 1, 1994, pending, which is a continuation-in-part of U.S. patent application Ser. No. 08/194,017, filed Feb. 9, 1994, which issued as U.S. Pat. No. 5,496,369 on Mar. 5, 1996, the contents of each of which are incorporated herein by reference.

BACKGROUND OF THE INVENTION

1. Field of the Invention

This invention relates generally to an apparatus for treating tinnitus, and in particular, to a prosthetic drug delivery device for microinfusing portions of drugs at geometrically separate locations of the patient's primary auditory cortex or the patient's thalamus.

2. Background of the Related Art

Tinnitus is a disorder where a patient experiences a sound sensation within the head ("a ringing in the ears") in the absence of an external stimulus. This uncontrollable ringing can be extremely uncomfortable and often results in severe disability. Tinnitus is a very common disorder affecting an estimated 15% of the U.S. population according to the National Institutes for Health, 1989 National Strategic Research Plan. Hence, approximately 9 million Americans have clinically significant tinnitus with 2 million of those being severely disabled by the disorder.

There are no treatments currently available that consistently eliminate tinnitus although many different types of treatments have been attempted. This wide variety of attempted treatments attests to the unsatisfactory state of current tinnitus therapy. Several more common attempts will be discussed below.

One approach involves suppression of abnormal neural activity within the auditory nervous system with various anticonvulsant or local anesthetic medications. Examples of such anticonvulsant medications include xylocaine and lidocaine which are administered intravenously. In addition, since the clinical impact of tinnitus is significantly influenced by the patient's psychological state, antidepressants, sedatives, biofeedback and counseling methods are also used. None of these methods has been shown to be consistently effective.

Another widely used approach to treating tinnitus involves "masking" undesirable sound perception by presenting alternative sounds to the patient using an external sound generator. In particular, an external sound generator is attached to the patient's ear (similar to a hearing aid) and the generator outputs sounds into the patient's ear. Although this approach has met with moderate success, it has several significant drawbacks. First, such an approach requires that the patient not be deaf in the ear which uses the external sound generator. That is, the external sound generator cannot effectively mask sounds to a deaf ear which subsequently developed tinnitus. Second, the external sound generator can be inconvenient to use and can actually result in loss of hearing acuity in healthy ears.

Yet another approach involves surgical resection of the auditory nerve itself. This more dangerous approach is usually only attempted if the patient suffers form large acoustic neuromas and tinnitus. In this situation, the auditory nerve is not resected for the specific purpose of eliminating tinnitus but is removed as an almost inevitable complication of large tumor removal. In a wide series of patients with tinnitus who underwent this surgical procedure of acoustic nerve resection, only 40% were improved, 10% were improved and 50% were actually worse.

An alternative and somewhat more successful approach involves electrical stimulation of the cochlea. In patients who have tinnitus and have received a cochlear implant, as many as half reported some improvement in their tinnitus after implantation. Round window stimulation has also been useful in improving tinnitus in selected patients. However, the success rate of this approach has also remained relatively low.

Prior to the nineteenth century, physicians and scientists believed the brain was an organ with functional properties distributed equally through its mass. Localization of specific functions within subregions of the brain was first demonstrated in the 1800s, and provided the fundamental conceptual framework for all of modern neuroscience and neurosurgery. As it became clear that brain subregions served specific functions such as movement of the extremities, and touch sensation, it was also noted that direct electrical stimulation of the surface of these brain regions could cause partial reproduction of these functions.

SUMMARY OF THE INVENTION

It is therefore an object of the invention to provide a therapeutic apparatus which can be placed in one of a patient's cerebral cortex or in the patient's thalamus to reduce the effects of tinnitus.

Another object of the invention is to provide a therapeutic apparatus which can be positioned in the brain such that electric discharges can be accurately delivered to geometrically dispersed locations in either the cortex or thalamus.

Another object of the invention is to provide a therapeutic device which allows a physician to physiologically test location and function of at least one to reduce or eliminate the patient's tinnitus.

Another object of the invention is to provide a therapeutic apparatus which can be positioned in the brain such that microinfusions of a drug that reduces abnormal neural activity, the latter leading to symptoms of tinnitus, such that the drug can be administered in geometrically dispersed locations in the patient's cortex or thalamus.

Another object of the invention is to provide a therapeutic device apparatus which can support a reservoir of the drug so that the microinfusions can be continuously administered.

One advantage of the invention is that it reduces or eliminates the effects of tinnitus.

Another advantage of the invention is that it can utilize a single electrode.

Another advantage of the invention is that it can utilize a single catheter.

Another advantage of the invention is that it penetrates the brain as opposed to resting on the brain surface, thus requiring significantly less current to stimulate localized areas of the cortex or the thalamus.

Another advantage of the invention is that it penetrates the brain thus requiring significantly lower doses of the drug and hence reduces unwanted side effects related to inadvertent treatment of surrounding tissue.

Another advantage of the invention is that the contacts are sufficiently closely arranged next to each other to provide high geometric resolution stimulation of the auditory cortex.

One feature of the invention is that it includes a penetrating longitudinal support or electrode.

Another feature of the invention is that it includes multiple contacts on the longitudinal support.

Another feature of the invention is that it includes a stimulation device.

Another feature of the invention is that each contact can separately introduce electrical discharges in the primary auditory cortex.

Another feature of the invention is that it utilizes a catheter to administer micro-infusions of the drugs to geometrically separate locations in the patient's cortex or thalamus.

Another feature of the invention is that the catheter includes an electrode for recording discharges in the patient's cortex or thalamus.

Another feature of the invention is that it utilizes a drug reservoir for containing reserve portions of the drug.

Another feature of the invention is that it can include a flexible wire multicontact electrode.

Another feature of the invention is that the flexible wire multicontact electrode is inserted into the brain using a rigid introducer.

Another feature of the invention is that a flat plastic plate attached to the longitudinal support (electrode) at the site of skull attachment helps position the prosthetic in the auditory cortex. The flat plastic plate having a cup to receive a sphere coupled to leads which interconnect the a speech processor.

These and other objects, advantages and features of the present invention will become more apparent from the following description of embodiments thereof taken in conjunction with the accompanying drawings.

DETAILED DESCRIPTION OF PREFERRED EMBODIMENTS

It is presumed that patients perceive tinnitus because neurons within the central auditory system (Auditory Cortex and/or Medial Geniculate Nucleus (MGN) of the Thalamus) are firing abnormally. By using sophisticated medical imaging and neurosurgical techniques discussed in U.S. patent application Ser. No. 08/194,017, now U.S. Pat. No. 5,496,369 the contents of which are incorporated herein by reference, specific regions in the brain can be targeted and the abnormal electrical activity blocked or masked with stimulating electrodes or with drugs delivered through precisely placed brain catheters.

The primary auditory region of the human brain is buried deep within the Sylvian fissure. It is not visible from the brain surface and its exact location varies slightly from one person to the next.

The minimal stimulation threshold for eliciting sound sensations was found to be 6 milliamperes, which is too high to be tolerated chronically and is thousands of times greater than currents found subsequently to be required to generate phosphenes in visual cortex using penetrating electrodes.

Recent advances in MRI and computer technology now allow detailed preoperative imaging of human auditory cortex.

An important aspect of the cochlear implant technology, which is now highly refined, involves transducing sound into complex electrical stimulation sequences. This large body of technical knowledge developed over the last twenty years will be directly applicable to the treatment of tinnitus via the auditory cortex therapeutic device.

Normal Hearing

Mechanisms of human hearing are reviewed briefly to provide a framework for discussion of the tinnitus masking system. The auditory system is composed of many structural components that are connected extensively by bundles of nerve fibers. The system's overall function is to enable humans to extract usable information from sounds in the environment. By transducing acoustic signals into electrical signals that can then be processed in the brain, humans are able to discriminate amongst a wide range of sounds with great precision.

Figure 1B:
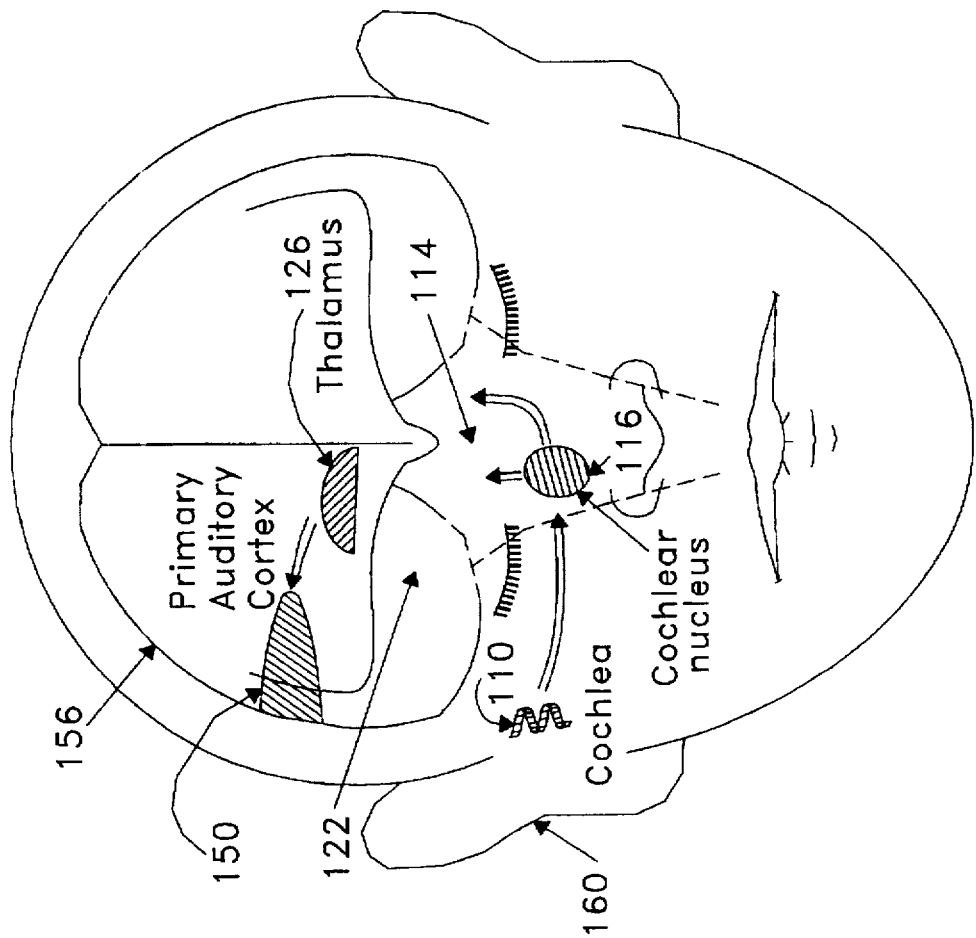
FIGS. 1A and 1B show the orientation of a patient's primary auditory cortex in relation to the patient's cochlea and cochlear nucleus.
Figure 1A:
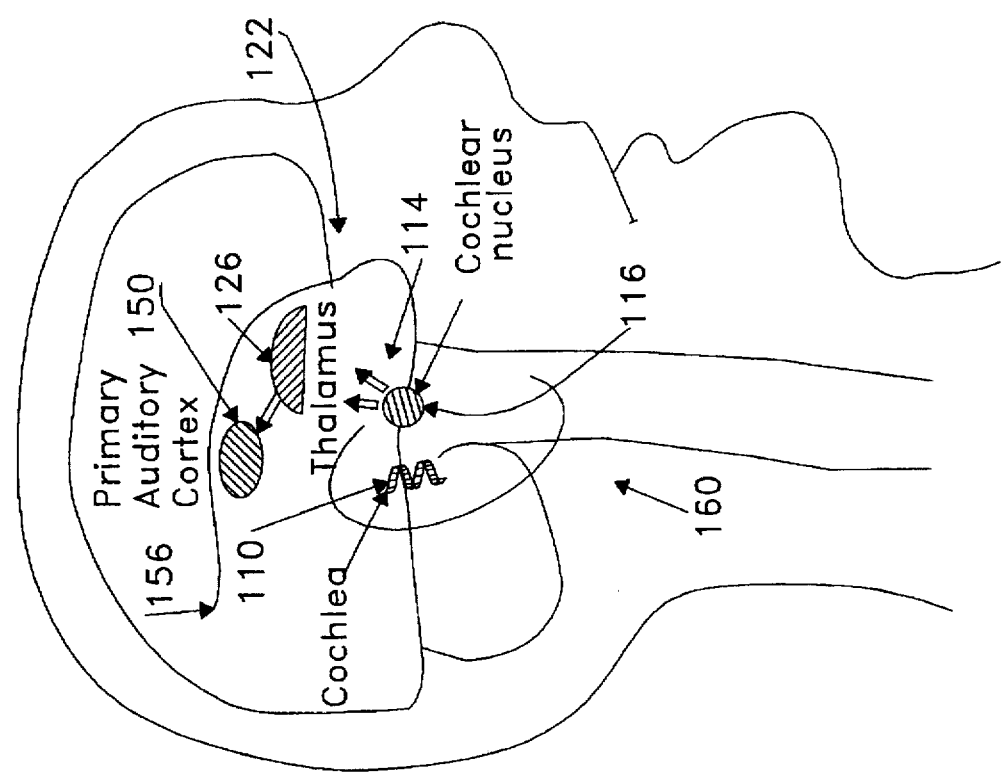

FIGS. 1A and 1B show a side and front view of areas involved in the hearing process. In particular, the normal transduction of sound waves into electrical signals occurs in cochlea 110, a part of the inner ear located within temporal bone (not shown). Cochlea 110 is tonotopically organized, meaning different parts of cochlea 110 respond optimally to different tones; one end of cochlea 110 responds best to high frequency tones, while the other end responds best to low frequency tones. Cochlea 110 converts the tones to electrical signals which are then received by cochlear nucleus 116. This converted information is passed from cochlea 110 into brain stem 114 by way of electrical signals carried along the acoustic nerve and in particular, cranial nerve VIII (not shown).

The next important auditory structure encountered is cochlear nucleus 116 in brain stem 114. As the acoustic nerve leaves the temporal bone and enters skull cavity 122, it penetrates brain stem 114 and relays coded signals to cochlear nucleus 116, which is also tonotopically organized. Through many fiber-tract interconnections and relays (not shown), sound signals are analyzed at sites throughout brain stem 114 and thalamus 126. The final signal analysis site is auditory cortex 150 situated in temporal lobe 156.

The mechanisms of function of these various structures has also been extensively studied. The function of cochlea 110 is the most well-understood and the function of auditory cortex 150 is the least understood. For example, removal of the cochlea 110 results in complete deafness in ear 160, whereas removal of auditory cortex 150 from one side produces minimal deficits. Despite extensive neural connections with other components of the auditory system, auditory cortex 150 does not appear to be necessary for many auditory functions.

Advanced imaging combined with an intraoperative stereotactic system now enable placement of penetrating electrodes into auditory cortex during routine epilepsy surgery without dissection of the Sylvian fissure.

Primary auditory cortex 150 in FIGS. 1A and 1B is tonotopically organized, meaning stimulation in different areas is likely to cause the patient to perceive different tones. These tones form the building blocks of complex sound phenomena such as speech. Tonotopic organization is a fundamental characteristic of the cochlea and cochlear nucleus as well, as discussed above. Auditory cortex 150, however, has its tonotopic map stretched across a larger volume of tissue (greater that twice the volume of cochlear nucleus 116). Greater tissue volume enables placement of a greater number of electrical contacts for a given tonotopic zone. This results in increased signal resolution and improved clarity of auditory sensation. Finally, because of anatomical differences, auditory cortex 150 can accommodate penetrating electrode arrays.

Stimulating Electrode

Figure 2A:
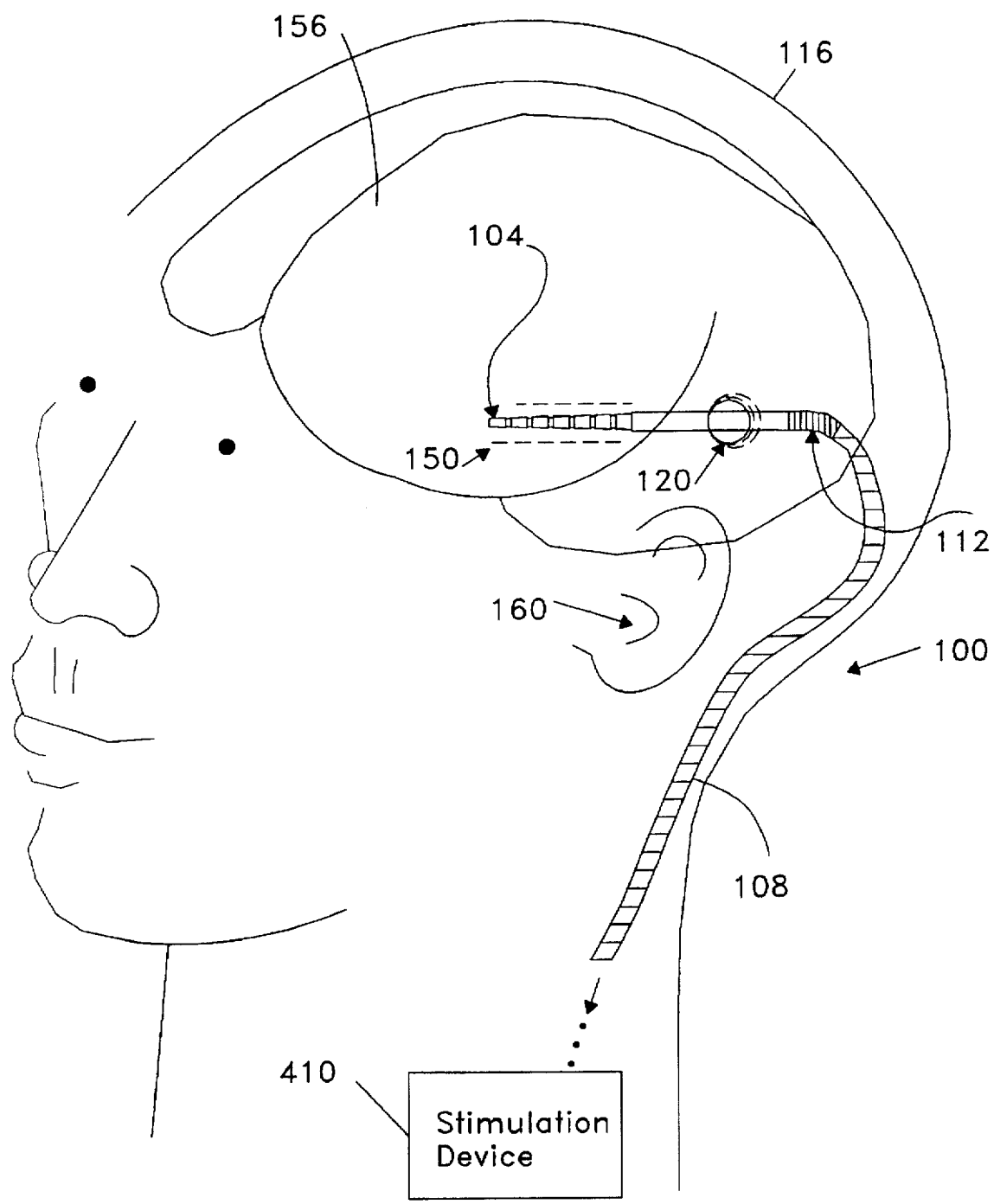
FIG. 2A shows a multi-contact recording/stimulating electrode system 100 for blocking and/or masking the abnormal electrical activity present in tinnitus patients according to one embodiment of the invention.

FIG. 2A shows a multi-contact recording/stimulating electrode system 100 for blocking and/or masking the abnormal electrical activity present in tinnitus patients according to one embodiment of the invention. In particular, system 100 includes a multi-contact stimulating/recording electrode 104 connected to cables 108 via connector 112. Cables 108 enter skull 116 at burr hole opening 120 of skull 115 and are connected to a stimulation device 410 positioned in subcutaneous tissue of axial skeleton (thorax or abdomen).

Figure 2B:
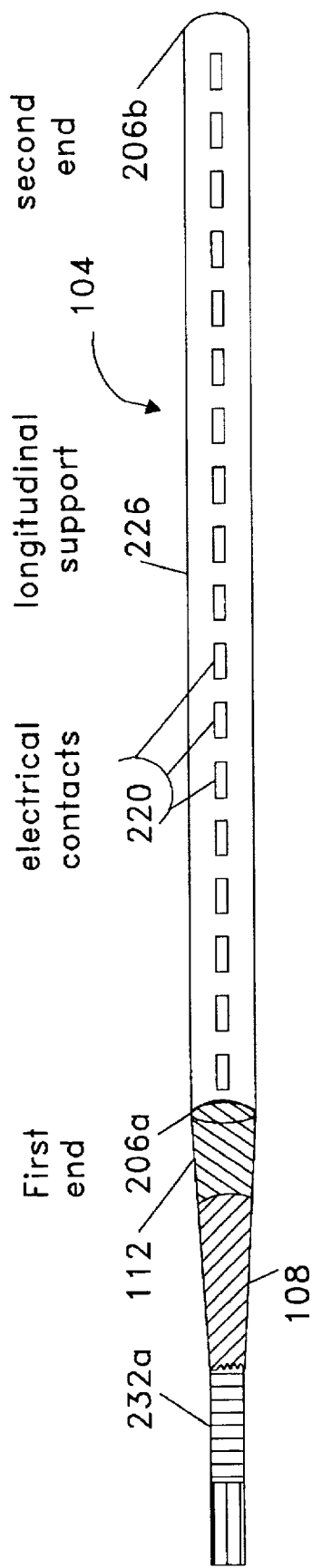
FIG. 2B shows a human cerebral cortex neural therapeutic device according to one embodiment of the invention.

FIG. 2B shows a closer view of multi-contact stimulating/ recording electrode 104 of electrode system 100. Electrode 104 has a first end 206a and a second end 206b which is blunt or smoothly curved. Electrode 104 has electrical contacts 220 along a longitudinal support 226. Support 226 can be anywhere from several millimeters long to several centimeters long. Electrical contacts 220 are small metal pads which can be separately electrically charged via respective wires 232 available at first end 206a. Wires 232 are coupled to stimulation device 410 (see FIGS. 2A and 4). Electrical contacts 220 are spaced approximately 10 micrometers to several millimeters apart and preferably approximately 50 to 150 micrometers apart. Each of electrical contacts 220 can separately introduce electrical discharges in the primary auditory cortex in accordance with electrical signals outputted from stimulation device 410. Application of a voltage to contacts 220 near first end 206a results in stimulating low (or high—to be determined by questioning the patient) tones in auditory cortex 150 (see FIGS. 1A and 1B), whereas application of a voltage to contacts 220 near second end 206b results in stimulation of high (or low) tones in auditory cortex 150.

Figure 3A:
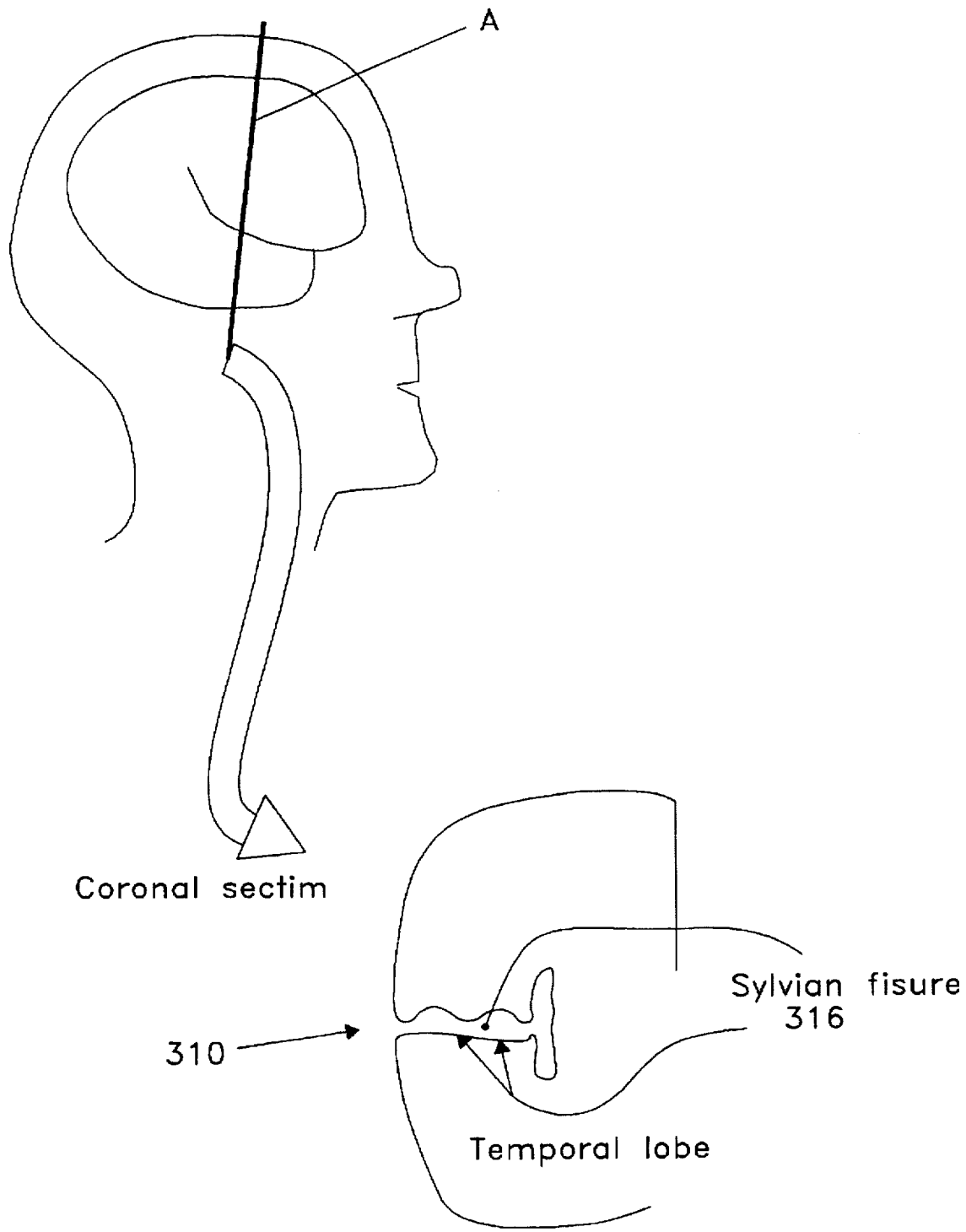
FIG. 3A shows a side view of a plane A which intersects a coronal section with a Sylvian fissure exposed.
Figure 3B:
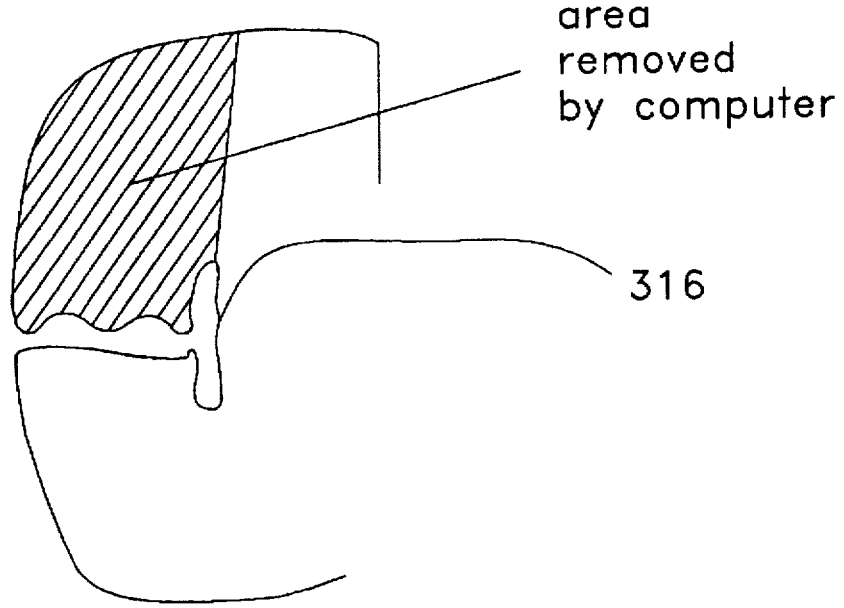
FIGS. 3B and 3C show the coronal section before and after tissue is digitally "peeled off" the Sylvian fissure.
Figure 3C:
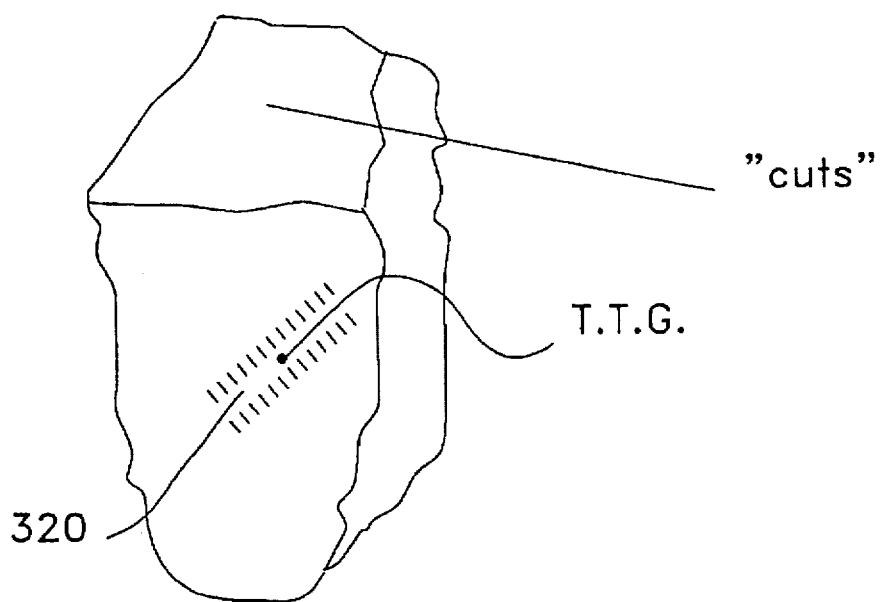

Electrode 104 is stereotaxically placed into the primary auditory cortex of the patient with tinnitus. This can be done using a standard stereotaxic head frame under local anesthesia. That is, the above discussed three dimensional computerized MRI reconstruction method of FIGS. 3A–3C is used to stereotaxically place electrode 104 within the targeted region of auditory cortex 150. Correct placement is confirmed by presenting a series of tones to the patient and mapping the tonotopic responses of the neurons along electrode 104.

In deaf patients, this mapping procedure is not possible, but mapping can still be carried out using microstimulation currents delivered to various contacts along electrode 104. The deaf patient describes the relative pitch of the sounds he or she perceives following stimulation, whereby the electrically stimulated location and parameters which most closely match the patient's tinnitus are determined. This approach could be used in the thalamus (MGN) as well, but the preferred embodiment involves implantation in the cortex. Regardless of whether or not stimulating electrode 104 is placed into the correct region of the cortex or into the correct region of the MGN, electrode 104 is coupled to stimulation device 410 via cables 108 and in particular, wires 232a.

Longitudinal support 226 can be a rigid support or a flexible wire with a rigid introducer which enables the physician to introduce electrode 104 into a patient's brain and then subsequently remove the rigid introducer thereby exposing electrical contacts 220 to auditory cortex 150. Support 226 can be one of the probes shown in FIGS. 3–5 in "Possible Multichannel Recording and Stimulating Electrode Arrays:.A Catalog of Available Designs" by the Center for Integrated Sensors and Circuits, University of Michigan Ann Arbor, Mich., the contents of which are incorporated herein by reference. Alternative electrodes such as Depthalon Depth Electrodes and interconnection cables from PMT Corporation 1500 Park Road, Chanhassen, Minn., 55317 could also be used as support 226 and electrical couplers between contacts 220 and a speech processor (410 in FIG. 4).

Electrical contacts 220 can operate as high impedance (megohms) contacts or low impedance (a few ohms to several thousand ohms) contacts. This enables the contacts to output a small (a few microamperes as opposed to a few milliamperes) current. High impedance contacts localize the potentials applied to the patient's primary auditory cortex to approximately a few hundred micrometers. The localization applied electric charges corresponds to the tonotopic spacing of nerve cell pairs.

Electrode 104 is arranged along a longitudinal direction of auditory cortex 150. However, auditory cortex 150 is located in the transverse temporal gyrus and is buried deep within the Sylvian fissure. Consequently, its location cannot be determined simply by looking at an exposed surface of the brain. Therefore, MRI imaging techniques must be employed to reveal the exact orientation of auditory cortex 150.

A single coronal image of an individual's brain cannot reveal the exact orientation of auditory cortex 150. However, for treatment of tinnitus, a standard coronal MRI provides a fairly good estimate as to the location of the target region, whether or not the target region is the auditory cortex or the thalamus. However, if more precise targeting is desired, a series of two dimensional images must be obtained and a resulting 3-D MRI image constructed. Once such an image is constructed, the digital data making up that image can be transformed to provide a view of the Sylvian fissure. This in turn exposes auditory cortex 150 as a mole-like mound. That is, tissue on top of the digital image can be "peeled off" to expose the sylvian fissure and consequently auditory cortex 150 "pops out" of the image. This process is described in "Three-dimensional In Vivo Mapping of Brain Lesions in Humans", by Hanna Damasio, MD, Randall Frank, the contents of which are incorporated herein by reference.

FIG. 3A shows a side view of a plane A which intersects a coronal section 310 as well as a view of coronal section 310 with Sylvian fissure 316 exposed. FIGS. 3B and 3C show coronal section 310 before and after tissue is digitally "peeled off" to expose auditory cortex 150. One or more resulting mounds 320 is revealed in FIG. 3C and this mound corresponds to auditory cortex 150 of FIG. 1B. Mound 320 does not appear until after tissue on the underside of Sylvian fissure 316 is reconstructed to provide the 3-D image. Once the exact location and orientation of mound 320 and consequently auditory cortex 150 have been determined using these 3-D MRI image processing techniques, electrode 104 can be accurately inserted into auditory cortex 150.

Figure 4:
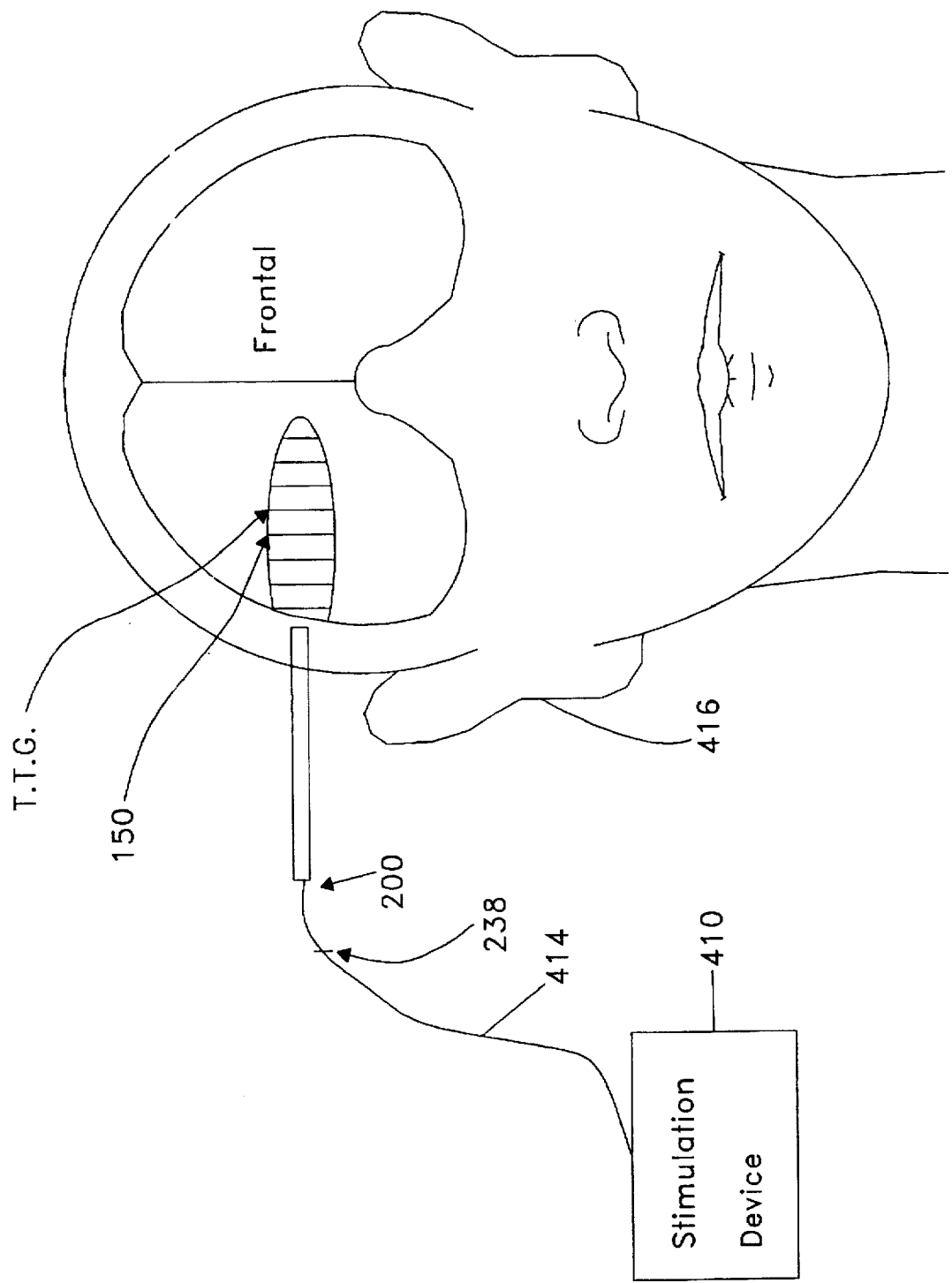
FIG. 4 shows a neural therapeutic device with a support having electrical contacts and its stimulation device.

FIG. 4 shows electrode 104 just prior to insertion into auditory cortex 150. In addition, FIG. 4 shows stimulation device 410 coupled to wires 232 via cable 108. Stimulation device 410 is a chronic electrical stimulation device. This stimulator device is well tested and widely available. Examples include chronic epidural stimulators made by Medtronics used for chronic back and leg pain and deep brain stimulators, as well as nearly all types of cochlear implants.

The above electrical implantation technique for tinnitus is quick and safe, e.g., over 100 auditory cortex region electrode implantations have been performed in patients being evaluated for medically intractable seizures as reported by a French epilepsy surgery group. In addition, since electrode 104 is placed in the exact site of presumed abnormal neuronal electrical activity, it is much more effective in disrupting or altering abnormal neuronal electrical activity, thereby eliminating tinnitus. Moreover, preliminary testing has shown that placement of electrode 104 within the central auditory system causes patients to perceive sounds, and this will likely be the case even in patients who are deaf from causes refractory to cochlear implantation. Also, stimulation in the auditory cortex does not impair hearing in tinnitus patients who do have good hearing.

Figure 5:
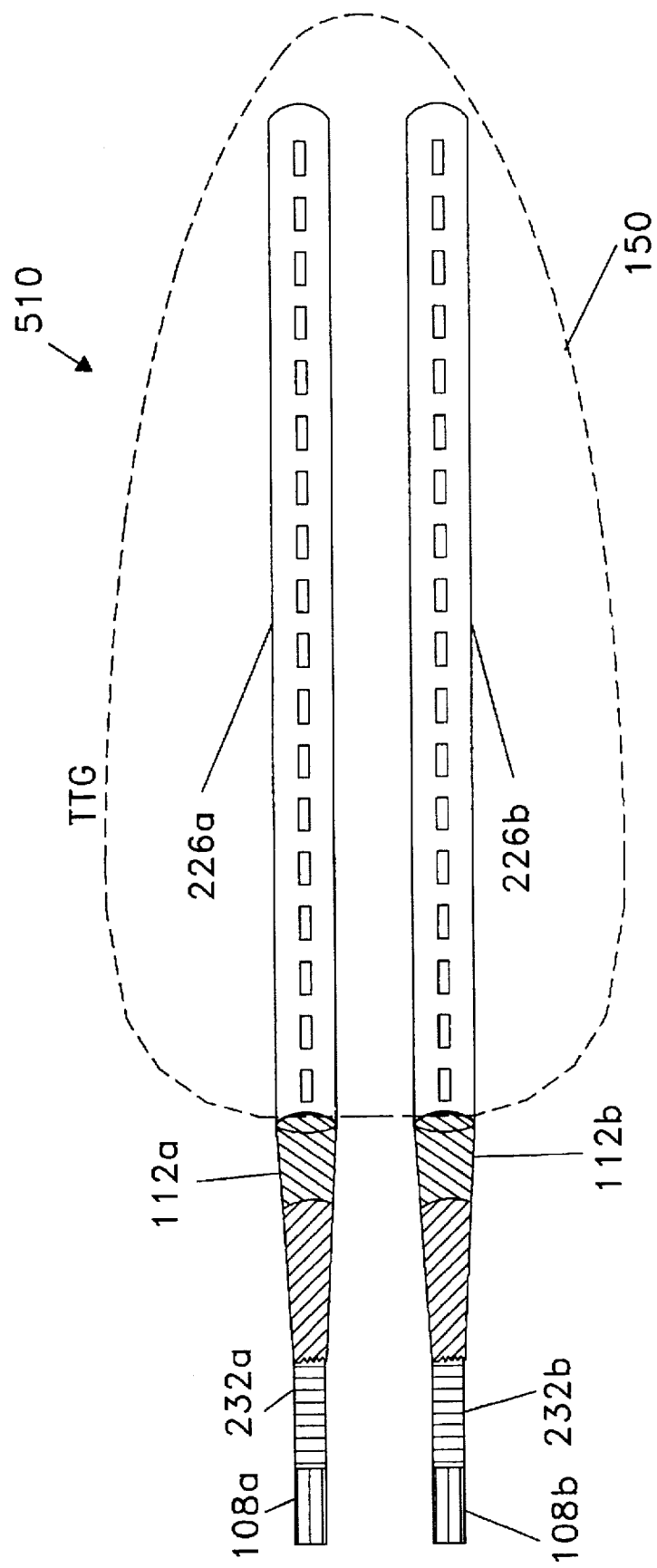
FIG. 5 shows a therapeutic device which includes two longitudinal supports according to another embodiment of the invention.

FIG. 5 shows an electrode 510 which includes two longitudinal supports 226a and 226b according to another embodiment of the invention. Although two supports are shown, three or more such supports could be used. Longitudinal support 226a is connected to cable 108a containing wires 232a via connector 112a and longitudinal support 226b is connected to cable 108b containing wires 232b via connector 112b. Cables 108a and 108b are again connected to stimulation device 410 as in FIG. 4.

Figure 6:
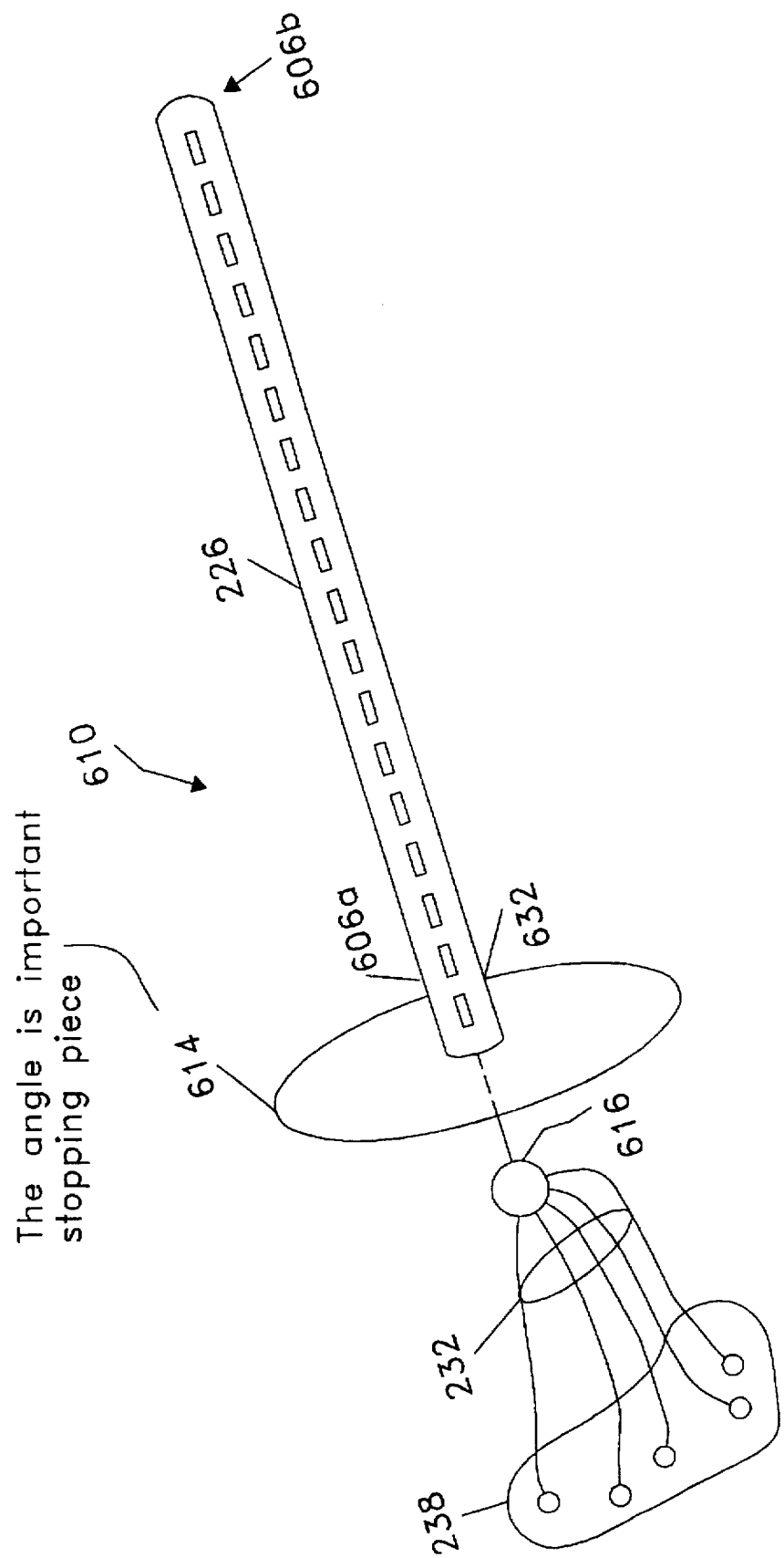
FIG. 6 shows a therapeutic device according to yet another embodiment of the invention.

FIG. 6 shows an electrode 610 according to yet another embodiment of the invention. In particular, FIG. 6 shows longitudinal support 226 with first end 606a and second end 606b. End 606a is arranged in the region of auditory cortex 150 with low tones (or high tones as previously discussed) and second end 606b is arranged in the region of auditory cortex 150 with high (or low) tones in a manner similar to first end 206a and second end 206b of FIG. 2B. Here, however, longitudinal support 226 has a sphere 616 which is stopped by a stopping piece 614. This enable the physician to insert longitudinal support 226 at a wide range of angles and yet secure electrode 610 once longitudinal support 226 has been inserted.

Figure 7A:
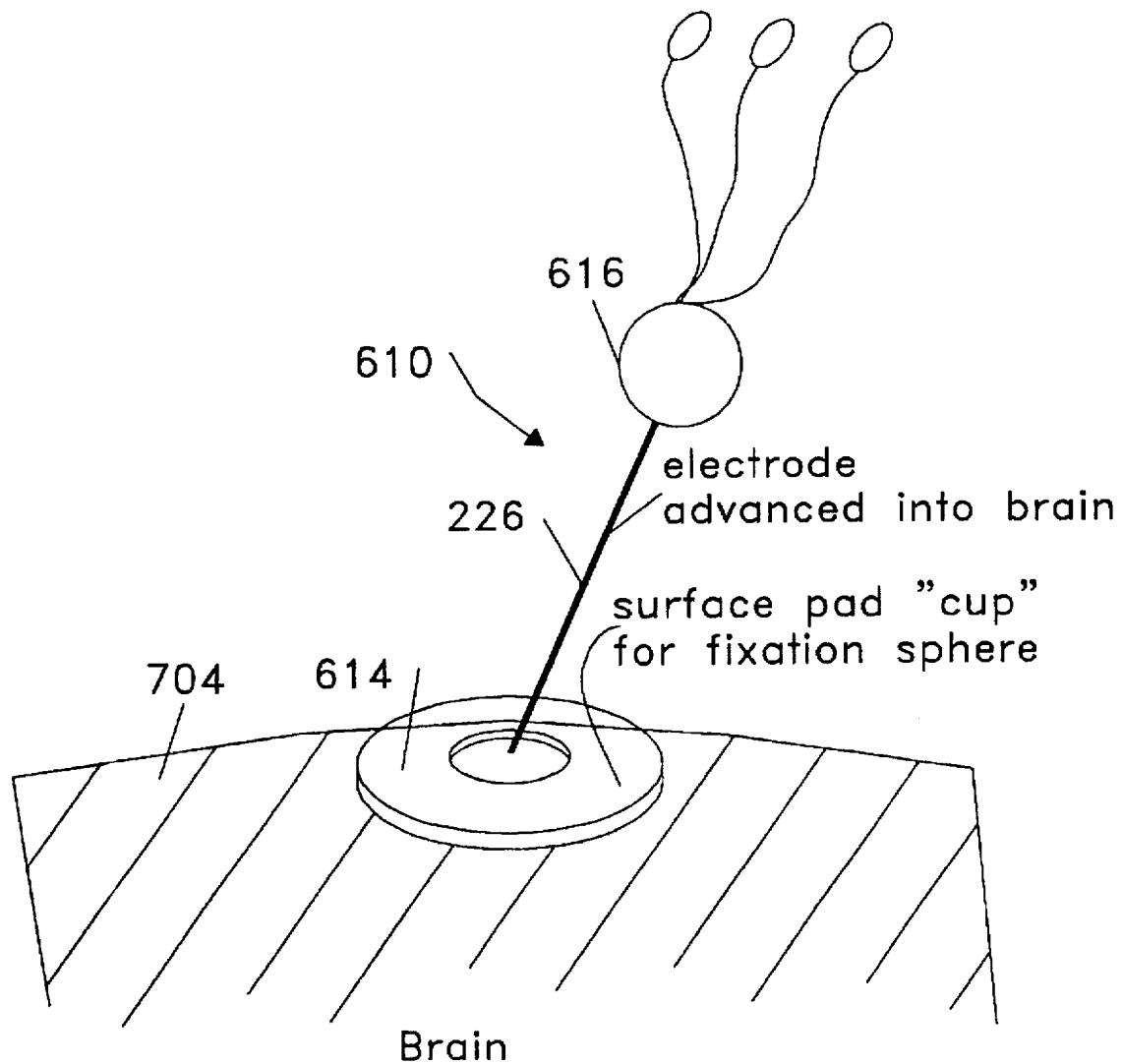
FIG. 7A shows the prosthetic of FIG. 6 as looking down on the patient's brain surface.
Figure 7B:
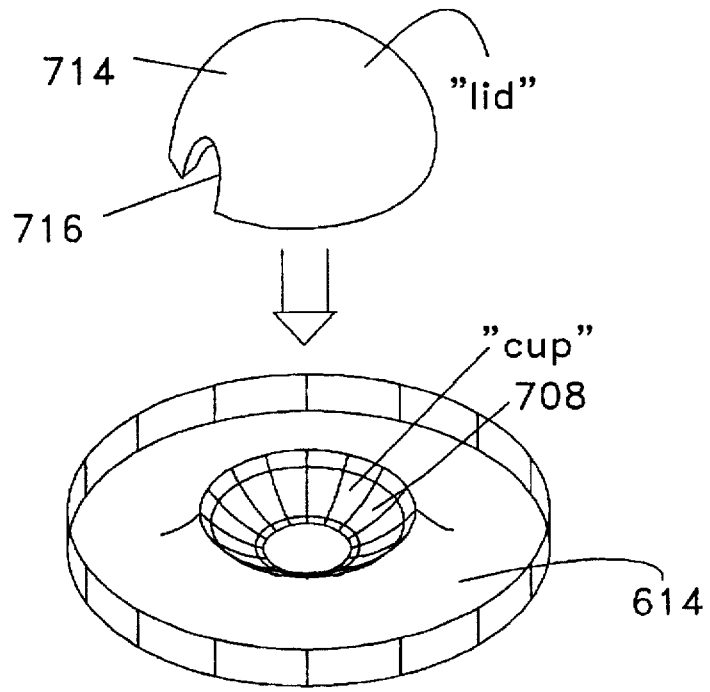
FIG. 7B shows a closer view of a stopping piece with a cup and a lid, and FIG. 7C corresponds to FIG. 7A with the support inserted.
Figure 7C:
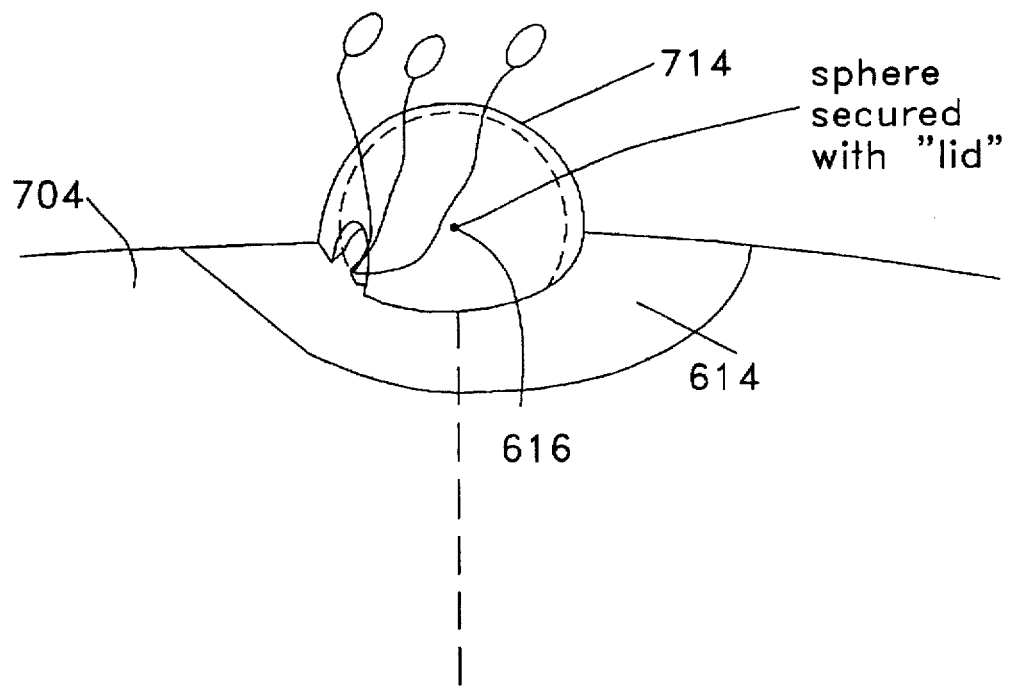

FIG. 7A shows electrode 610 of FIG. 6 as looking down on the patient's brain surface 704. FIG. 7B shows a closer view of stopping piece 614 with a cup 708 and a lid 714 with a notch 716 for passing leads 232. FIG. 7C corresponds to FIG. 7A with support 236 inserted into surface 704 and sphere 616 resting in cup 708. FIG. 7C also shows lid 716 covering sphere 616 with leads 232 extending out of notch 716.

Figure 8:
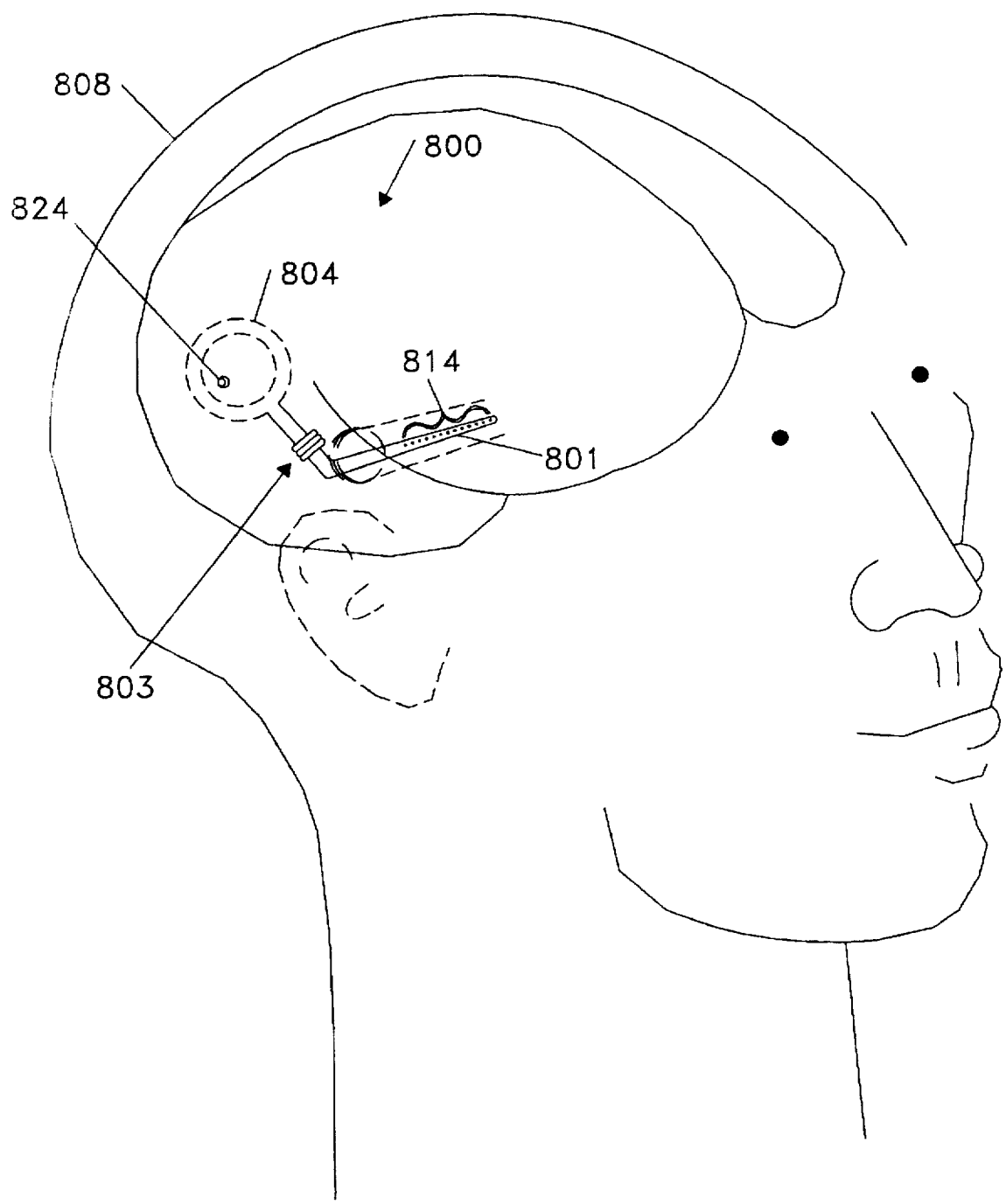
FIG. 8 shows another embodiment of the invention involving drug-infusion into regionally targeted locations within the brain according to another embodiment of the invention.

FIG. 8 shows another embodiment of the invention involving drug-infusion into regionally targeted locations within the brain. The alternative drug-infusion treatment strategy relies on the same principal of regionally targeted treatment within the brain, but employs a different effector to eliminate the abnormal neural activity causing tinnitus. Namely, a small drug infusion catheter 801 is stereotaxically placed into either the auditory cortex or thalamus (MGN) and microinfusions of various drugs that block abnormal neural activity are infused into the targeted locations.

Referring in more detail to FIG. 8, a drug infusion catheter-recording device 800 is connected to an injectable (rechargeable) drug reservoir-pump 804 via connector 803 which is secured with sutures widely used in neurosurgery. Pump 804 is secured to the patient's skull 808 under the scalp and is not exposed to the external environment. Pump 804 has a valve 824 which can be accessed externally so that additional drugs can be injected via a syringe (not shown) without reopening the patient's scalp. Catheter 801 has multiple-ports 814 from which the drugs are microinfused into the targeted brain regions.

Figure 9:
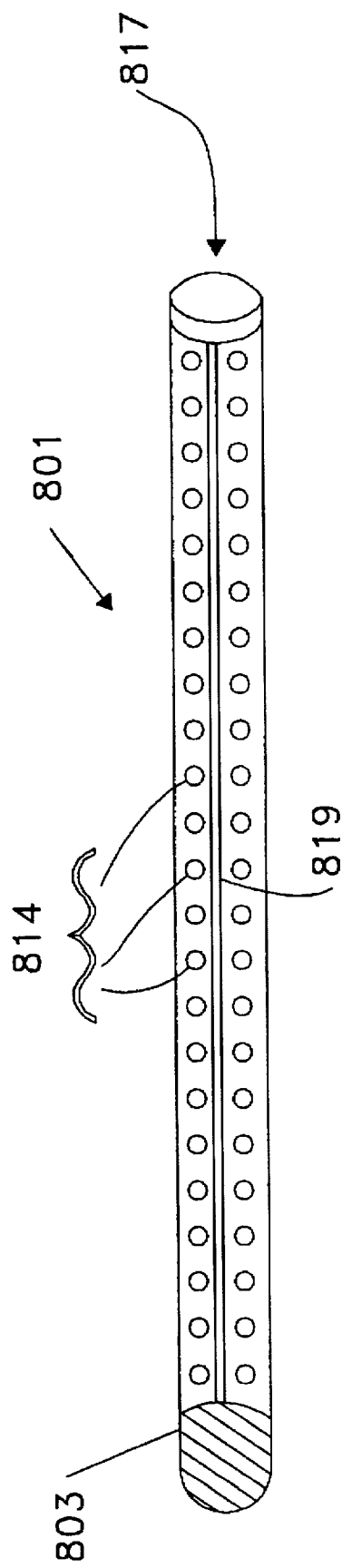
FIG. 9 shows a closer view of a catheter with ports or openings.

FIG. 9 shows a closer view of catheter 801 with ports or openings 814 are arranged at discrete locations along catheter 801. Catheter 801 can be made, for example, of silastic such as the catheters sold by Radionics, Codman, and Medtronics. Catheter 801 may be elongate and at least substantially cylindrical as depicted in FIG. 9 but need not have a circular cross-section 817 and instead can be flat, elliptical or any other shape which facilitates broader diffusion of the drug. Catheter 801 can include a small embedded recording-stimulating electrode 819 which can be connected to stimulation device 410 so that catheter 801 can be properly positioned. Electrophysiologic recording data (recorded on a recording device) from this special catheter electrode will provide physiologic confirmation of proper catheter position in auditory cortex. The diameters of ports (or openings) 814 can be approximately between 10 micrometers and several millimeters and preferably between approximately 40 micrometers and 1 millimeter. The centers of ports 814 can also be tens of micrometers apart to millimeters apart and the spacing need not be uniform.

Pumps manufactured by Medtronics and Alzet can serve as injectable drug reservoir-pump 804. Examples of drugs that could be infused include anticonvulsants such as dilantin, inhibitory neurotransmitters such as γ-aminobutyric acid (GABA) and local anesthetics such as lidocaine. In high enough concentrations, these compounds should block abnormal neuronal discharges. By delivering the drugs to the specific central nervous system target, significantly higher concentrations of the drug reach their target without exposing non-targeted surrounding tissue, as compared to the concentrations which could be delivered by simply administering the same drug systemically, e.g. orally or intravenously. Consequently, this strategy should result in marked improvement in efficacy while avoiding toxic side effects.

The precise amount of drug infusion depends on the type of drug but can be determined at the outset of implantation. In particular, catheter 801 is initially inserted into the targeted location in the manner described above for insertion of electrode 104. The patient is then asked if there is any noticeable reduction in ringing due to the tinnitus as the amount of drug infusion is manually adjusted. The amount of infusion is that amount which is required to eliminate the ringing. Once the amount is determined, the appropriate chronic diffusion pump 804 is connected to catheter 801 and all incisions are closed. Post-operative modifications of infusion rates can be carried out using percutaneous radio control techniques, e.g., Medtronics.

As mentioned above, the alternative drug-infusion treatment strategy relies on the same electrode placement principals as described above with respect to FIGS. 3A–3C. Namely, a series of images must again be obtained and a resulting 3-D MRI image constructed. Once the image is constructed, the digital data making up that image can be transformed to provide a view of the Sylvian fissure. This in turn exposes auditory cortex 150 as a mole-like mound. Again, tissue on top of the digital image can be "peeled off" to expose the Sylvian fissure and consequently auditory cortex 150 "pops out" of the image.

Numerous additional modifications and variations of the present invention are possible in light of the above teachings. It is therefore understood that the invention may be practiced otherwise than as specifically claimed.

What is claimed is:

1. A neural therapeutic apparatus for treatment of a patient with tinnitus, comprising:

a drug reservoir-pump for containing and pumping a drug, wherein said drug is capable of reducing abnormal neural activity associated with tinnitus; and a drug delivering catheter for arrangement in the patient's auditory, cortex or thalamus, said drug delivering catheter operatively connected to said drug reservoir-pump, and said drug delivering catheter having a plurality of ports, each of said plurality of ports capable of outputting said drug to predetermined geometric locations within said one of the patient's auditory, cortex and thalamus.

2. The neural therapeutic apparatus as claimed in claim 1, further comprising:

a stimulation device for outputting electrical signals; and a stimulating and recording electrode arranged in said drug delivering catheter, said electrode having a plurality of electrical contacts electrically coupled to said stimulation device, and each of said plurality of electrical contacts outputting one or more electrical discharges in accordance with said electrical signals, wherein each of said electrical contacts is capable of receiving electrical discharges in said one of the patient's auditory, cortex and thalamus, and wherein said electrical discharge output blocks abnormal neural activity and alleviates the symptoms of tinnitus.

3. The neural therapeutic apparatus as claimed in claim 1, wherein said drug capable of reducing abnormal neural activity comprises a neurotransmitter inhibitor.

4. The neural therapeutic apparatus as claimed in claim 1, wherein said drug capable of reducing abnormal neural activity comprises an anticonvulsant.

5. The neural therapeutic apparatus as claimed in claim 1, wherein said drug capable of reducing abnormal neural activity comprises dilantin or γ-aminobutyric acid.

6. The neural therapeutic apparatus of claim 1, wherein said drug delivering catheter comprises silastic material.

7. The neural therapeutic apparatus of claim 1, wherein said drug delivering catheter has a cross-sectional shape which is substantially circular or substantially elliptical.

8. The neural therapeutic apparatus of claim 1, wherein said plurality of ports are arranged at discrete locations on said drug delivering catheter.

9. The neural therapeutic apparatus of claim 8, wherein each of said plurality of ports are substantially circular and are from about 10 micrometers to about 2 millimeters in diameter, and wherein said plurality of ports are spaced from about 6 micrometers to about 2 millimeters apart.

10. The neural therapeutic apparatus of claim 9, wherein the centers of each of said plurality of ports are separated by a distance in the range of from about 20 micrometers to about 2 millimeters.

11. A neural therapeutic apparatus for implantation in a target zone of a patient's brain, comprising:

a reservoir-pump for containing a drug, said drug capable of reducing abnormal neural activity, associated with tinnitus;

a catheter for delivering said drug to the target zone of the patient's brain, said catheter operably connected to said reservoir-pump, and comprising one or more stimulating and recording electrodes;

a stimulation device for outputting electrical signals to said one or more electrodes, said electrodes outputting electrical discharges in accordance with said electrical signals, wherein said outputted electrical discharges block abnormal neural activity; and a recording device operably connected to said one or more electrodes, said recording device capable of recording electrophysiologic data received by said one or more electrodes, from said target zone of the patient's brain.

12. The neural therapeutic apparatus of claim 11, wherein said catheter includes a plurality of ports, each of said plurality of ports capable of outputting said drug to a geometrically separate, predetermined location within said target zone of the patient's brain.

13. The neural therapeutic apparatus of claim 11, wherein said electrode has a plurality of electrical contacts, each of said plurality of electrical contacts electrically coupled to said stimulation device, with each of said plurality of electrical contacts capable of outputting electrical discharges to said target zone of the patient's brain, wherein each of said plurality, of electrical contacts is further capable of receiving electrical discharges for recording as electrophysiologic data from said target zone of the patient's brain.

14. The neural therapeutic apparatus of claim 11, wherein said reservoir-pump includes a recharging valve, and wherein said recharging valve is externally accessible.

15. The neural therapeutic apparatus of claim 11, wherein said reservoir-pump is adapted for attachment to the patient's head, and wherein said reservoir-pump is adjustable by a radio control means.

16. The neural therapeutic apparatus of claim 11, wherein said drug is selected from the group consisting of an anticonvulsant, a neurotransmitter and a local anesthetic.

17. A neural therapeutic drug delivery apparatus for implantation in a target zone of a patient's brain, comprising:

means for delivering a drug to said target zone of the patient's brain, said drug capable of reducing abnormal neural activity associated with tinnitus;

means for outputting electrical discharges to said target zone of the patient's brain; and means for receiving electrical discharges from said target zone of the patient's brain.

18. The neural therapeutic drug delivery, apparatus of claim 17, wherein said means for outputting electrical discharges and said means for receiving electrical discharges comprise one or more stimulating and recording electrodes, and said means for delivering said drug comprises a catheter comprising one or more ports capable of outputting said drug to one or more predetermined, separate locations within said target zone of the patient's brain.

19. The neural therapeutic drug delivery apparatus of claim 18, wherein said means for delivering said drug further comprises a radio-controlled pump connected to said catheter, and wherein said target zone is an auxiliary cortex or a medial geniculate nucleus of a thalamus.

* * * * *